(12) United States Patent
Wiegel et al.

(10) Patent No.: US 7,922,695 B2
(45) Date of Patent: Apr. 12, 2011

(54) DRUG DELIVERY PUMP DRIVE USING LINEAR PIEZOELECTRIC MOTOR

(75) Inventors: Christopher Wiegel, Sunnyvale, CA (US); Marco De Polo, San Mateo, CA (US); Steven Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 383 days.

(21) Appl. No.: 11/874,417

(22) Filed: Oct. 18, 2007

(65) Prior Publication Data

US 2009/0105650 A1  Apr. 23, 2009

(51) Int. Cl.
*A61M 37/00* (2006.01)
(52) U.S. Cl. ........ 604/155; 604/107; 604/108; 604/209; 604/156; 604/165.04; 604/211; 604/31; 604/134; 604/151; 604/256; 310/311; 310/328
(58) Field of Classification Search ............ 310/311, 310/328; 604/107, 108, 155, 209, 156, 165.04, 604/211, 31, 134, 151, 256
See application file for complete search history.

(56) References Cited

U.S. PATENT DOCUMENTS

| | | | | |
|---|---|---|---|---|
| 3,745,843 A | * | 7/1973 | Hetzel | 74/128 |
| 3,868,861 A | * | 3/1975 | Scholin | 74/129 |
| 3,903,436 A | * | 9/1975 | Moriya | 310/339 |
| 3,970,420 A | * | 7/1976 | Goto | 431/255 |
| 4,169,984 A | * | 10/1979 | Parisi | 310/323.18 |
| 4,685,903 A | * | 8/1987 | Cable et al. | 604/154 |
| 4,760,939 A | * | 8/1988 | Ball et al. | 222/23 |
| 4,871,939 A | * | 10/1989 | Clouser | 310/332 |
| 5,237,236 A | | 8/1993 | Culp | |
| 5,562,015 A | * | 10/1996 | Zinck | 81/57.13 |
| 6,147,435 A | | 11/2000 | Fujimura | |
| 6,203,528 B1 | | 3/2001 | Deckert et al. | |
| 6,249,717 B1 | | 6/2001 | Nicholson et al. | |
| 6,375,638 B2 | | 4/2002 | Nason et al. | |
| 6,656,158 B2 | | 12/2003 | Mahoney et al. | |
| 6,723,072 B2 | | 4/2004 | Flaherty et al. | |
| 6,726,678 B1 | | 4/2004 | Nelson et al. | |
| 6,811,548 B2 | | 11/2004 | Jeffrey | |
| 6,940,209 B2 | | 9/2005 | Henderson | |
| 7,119,478 B1 | * | 10/2006 | Mentesana | 310/328 |

(Continued)

FOREIGN PATENT DOCUMENTS

DE  102005004498 A1  8/2006
(Continued)

OTHER PUBLICATIONS

Lopez, Jose F., "Modeling and Optimizationof Ultrasonic Linear Motors", Ecole Polytechnique Federale De Lausane, Theses No. 3665 (2006)

(Continued)

*Primary Examiner* — Nicholas D Lucchesi
*Assistant Examiner* — Scott Medway
(74) *Attorney, Agent, or Firm* — Dinsmore & Shohl LLP

(57) ABSTRACT

A drug delivery pump drive which uses a linear piezoelectric motor to advance a syringe piston to deliver a liquid drug and a method thereof are disclosed. The pump drive, provided in a drug delivery pump, provides silent operation and very low energy consumption compared to electric motor-based drives. The small size of the motor helps also to reduce overall size of the pump drive and the resulting drug deliver pump.

12 Claims, 6 Drawing Sheets

U.S. PATENT DOCUMENTS

| | | | |
|---|---|---|---|
| 7,170,214 B2 | 1/2007 | Henderson et al. | |
| 7,193,521 B2 | 3/2007 | Moberg et al. | |
| 7,456,550 B2 * | 11/2008 | Deck | 310/328 |
| 2004/0220551 A1 | 11/2004 | Flaherty et al. | |
| 2005/0177111 A1 | 8/2005 | Ozeri et al. | |
| 2008/0051711 A1 * | 2/2008 | Mounce et al. | 604/131 |
| 2008/0097326 A1 * | 4/2008 | Moberg et al. | 604/155 |
| 2008/0269570 A1 * | 10/2008 | Leung et al. | 600/300 |
| 2009/0124994 A1 * | 5/2009 | Roe | 604/500 |

FOREIGN PATENT DOCUMENTS

| | | |
|---|---|---|
| WO | 02071592 A2 | 9/2002 |
| WO | 2008024808 A2 | 2/2008 |

OTHER PUBLICATIONS

Newscale Technologies Webpage, htttp://www.newscaletech.com/nonmagnetic.html, 2006.

Internet Archive Wayback Machine record of New Scale Technologies Webpage, http://www.web.archive.org/web/*/http://www.newscaletech.com/nonmagnetic.html, Mar. 28, 2007.

Preliminary Report on Patentability, Application PCT/EP2008/008791, Date of Issuance of this report Apr. 20, 2010, 10 pages.

* cited by examiner

DRUG DELIVERY PUMP DRIVE USING LINEAR PIEZOELECTRIC MOTOR

FIELD OF THE INVENTION

The present invention is generally related to drug delivery pumps, and in particular to a drug delivery pump drive using a linear piezoelectric motor to advance a syringe piston to deliver a liquid drug.

BACKGROUND OF THE INVENTION

Typically miniature drug delivery pumps use an electric motor and a system of many gears to reduce the high speed motors down to a slower speed. The slower speed provides the precision needed to control the very small doses of a liquid drug being delivered by means of an advancing lead screw and nut moving the syringe piston. Due to the above performance requirements, such miniature drug delivery pump use an expensive high quality electric motor and the associated high quality gears, therefore making such pumps expensive and generally not disposable in nature. In addition, concealment under clothing is problematic due to the relative size of the motor and the noise generated during operation.

SUMMARY OF THE INVENTION

It is against the above background that the present invention provides a drug delivery pump drive which uses a linear piezoelectric motor to advance a syringe piston to deliver a liquid drug. The pump drive, provided in a drug delivery pump, provides silent operation and very low energy consumption compared to electric motor-based drives. The small size of the motor helps also to reduce overall size of the pump drive and the resulting drug deliver pump.

In one embodiment, a drive system used to dispense a liquid drug from a drug container having a piston is disclosed. The drive system comprises a lead screw having a rotational axis and operably connected to the piston; a ratchet wheel provided along the rotational axis and operably connected to the lead screw to rotate the lead screw about the rotational axis; a piezoelectric motor having a shaft, a nut engaging the shaft, and piezoelectric elements configured to produce reciprocating linear and rotational motion of the shaft relative to the nut adjacent the rotational axis; and a pawl operably connected to the shaft and engaging the ratchet wheel such that the reciprocating linear motion of the shaft is converted into unidirectional rotary motion of the ratcheted wheel about the rotational axis which moves the lead screw and advances the piston to dispense the liquid drug from the drug container. Completion of the cycle may be confirmed either by sensing the motor shaft has reached the limits of its travel or by the successful advancement of the ratchet by one tooth.

In another embodiment, a method for dispensing a liquid drug from a drug container having a piston is disclosed. The method comprises providing a lead screw having a rotational axis and operably connected to the piston; providing a ratchet wheel along the rotational axis and operably connected to the lead screw to rotate the lead screw about the rotational axis; providing a piezoelectric motor having a shaft, a nut engaging the shaft, and piezoelectric elements configured to produce reciprocating linear motion of the shaft relative to the nut adjacent the rotational axis; and providing a pawl operably connected to the shaft and engaging the ratchet wheel such that the reciprocating linear motion of the shaft is converted into unidirectional rotary motion of the ratcheted wheel about the rotational axis which moves the lead screw, wherein moving the lead screw advances the piston dispensing the liquid drug from the drug container.

Another embodiment discloses a drive system in which the motor shaft is held to rotate but not translate while the motor body is allowed to translate but not rotate. The drive system comprises a lead screw having a rotational axis and operably connected to the piston; a piezoelectric motor having a threaded shaft, a threaded motor body engaging the shaft, and piezoelectric elements configured to produce reciprocating linear and rotational motion of the shaft relative to the nut; a housing to constrain the shaft to rotate while constraining the motor body to translate; a connection between the motor shaft and lead screw to transmit the rotational movement of the shaft to the lead screw; a nut engaging the lead screw and operably connected to the piston; whereby as the motor is activated, the shaft outputs only rotary motion which causes the nut to advance along the lead screw, advancing the piston and dispensing liquid drug from the drug container.

These and other features and advantages of the invention will be more fully understood from the following description of various embodiments of the invention taken together with the accompanying drawings.

BRIEF DESCRIPTION OF THE DRAWINGS

The following detailed description of the various embodiments of the present invention can be best understood when read in conjunction with the following drawings, where like structure is indicated with like reference numerals and in which.

DETAILED DESCRIPTION

In the following description of the embodiments of the invention, skilled artisans appreciate that elements in the figures are illustrated for simplicity and clarity and have not necessarily been drawn to scale. For example, the dimensions of some of the elements in the figures may be exaggerated relative to other elements to help to improve understanding of embodiment(s) of the present invention. Accordingly, the drawings are merely schematic representations, intending to depict only typical embodiments of the invention, and there-
} fore should not be considered as limiting the scope of the invention. The invention will be described with additional specificity and detail through the accompanying drawings. The description of the invention may contain, for example, such descriptive terms as up, down top, bottom, right or left. These terms are meant to provide a general orientation of the parts of the invention and are not meant to be limiting as to the scope of the invention.

Figure 1:
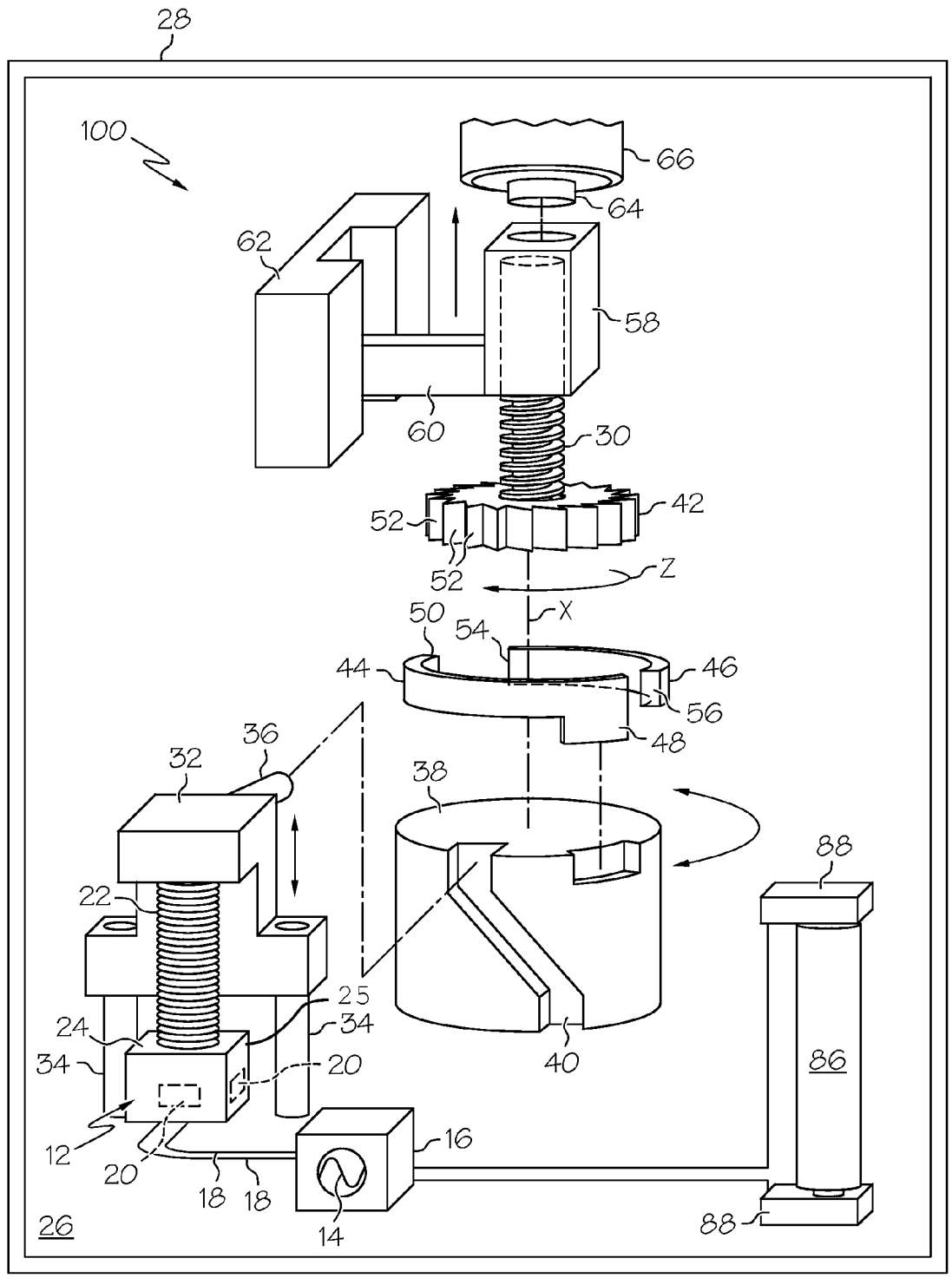
FIG. 1 is an exploded perspective view of a drug delivery pump drive embodiment using a linear piezoelectric motor positioned parallel to an axis of rotation of a lead screw arrangement according to the present invention.

With reference to FIG. 1, an embodiment of a drug delivery pump drive 100 using a linear piezoelectric motor 12 is shown. It is to be appreciated that such a drug delivery pump drive 100 is suitable for use in an infusion pump application to accurately pump a liquid drug. A suitable linear piezoelectric motor is described in U.S. Pat. No. 6,940,209, the disclosure of which is herein incorporated fully by reference. In one embodiment, the motor 12 has a 3.5×3.5×15 mm footprint, which is about 20% the size of conventional electrical micromotors. The motor 12 provides an adjustable stroke that can be precisely controlled in a range up to about 4 mm and in a speed range up from about 0.001 to about 3 mm/s. Typical input power (moving) is about 300 mW.

In use, the application of a drive signal 14 from a controller 16 via wires 18 causes piezoelectric elements 20 in the motor 12 to vibrate or be driven through a range of motion which includes friction between contacting and constrained motor members, such as a threaded rod or shaft 22 and a motor body 24 which acts like a nut 25. In particular, the friction generated between the shaft 22 and the motor body 24, which houses the piezoelectric elements 20, causes the shaft 22 to rotate about the motor body 24, thereby producing the linear movement of the shaft 22 relative to the motor body 24. As the motor body 24 in the illustrated embodiment is fixed to a base 26 within a drug delivery or infusion pump 28, the shaft 22 will advance and apply a force axially (i.e. pushing) in either direction (e.g., up and down) depending on the drive signal 14. In one embodiment, the push force applied by the shaft is about 2 Newtons using a 100 VAC RMS sinusoidal drive signal.

In the illustrated embodiment of FIG. 1, it is to be appreciated that the shaft 22 of the motor 12 is mounted parallel to a rotational axis X of a lead screw 30. The motor 12 drives a linear slider 32 in both directions (e.g., up and down) parallel to the rotational axis X. The slider 32 is mounted slidably to a pair of braces 34 which is also fixed to the base 26. The slider 32 has an integral pin 36. A cam 38 is mounted rotatably to the base 26 and located coaxially to the lead screw 30. It is to be appreciated that the cam 38 may rotate in both directions (e.g., right and left) about the rotational axis X. The cam 38 has an integral track 40 that receives the pin 36. The track 40 is helical or angled from the rotational axis X, so that oscillating axial motion (e.g., up and down) of the pin 36 causes oscillating radial movement of the cam 38 about the rotational axis X.

A ratchet wheel 42 is located coaxially and fixed at an end of the lead screw 30. The ratchet wheel 42 and/or the lead screw 30 is mounted rotatably and coaxially to the cam 38. A pair of pawls 44, 46 allows the ratchet wheel 42 to be rotated in only one direction designated by symbol Z about the rotational axis X. The first pawl 44 is mounted at a first end 48 to the cam 38 and is located adjacent the ratchet wheel 42 such that a free end 50 of the first pawl 44 cooperates with the saw-like teeth 52 of the ratchet wheel 42. The second pawl 46 is fixed at first end 54, such as for example, to the base 26, and located also adjacent the ratchet wheel 42 such that a free end 56 cooperated with the teeth 52 of the ratchet wheel 42 and prevents the ratchet wheel from freely rotating in the opposite direction to the direction Z.

In the provided drive arrangement of the first illustrated embodiment, it is apparent that the oscillating (e.g., up and down) movement of the shaft 22 of the motor 12 about the motor body 24 causes the incrementing of the ratchet wheel 42 one tooth at a time. The tooth-by-tooth rotation of the ratchet wheel 42 causes the lead screw 30 to also rotate about the rotational axis X. As shown, the lead screw 30 is only free to rotate and is prevented from translating axially. A threaded nut 58 engages the lead screw 30.

The threaded nut 58 is provided with a projection or key portion 60 which is situated in a slot or keyway 62 that is mounted, for example, to the base 26. In this manner, the nut is prevented by the keyway 62 from rotating about the rotational axis X with the ratchet wheel 42 and lead screw 30 but is free to translate incrementally along axis X. The incremental advancement of the threaded nut 58 along the keyway 62 causes a plunger or piston 64 to be pushed into a syringe-like drug cartridge or container 66. The pushing of the piston 64, via incremental advancement of the nut 58, causes a liquid drug to be expelled from the container 66 in a controlled manner.

Figure 2:
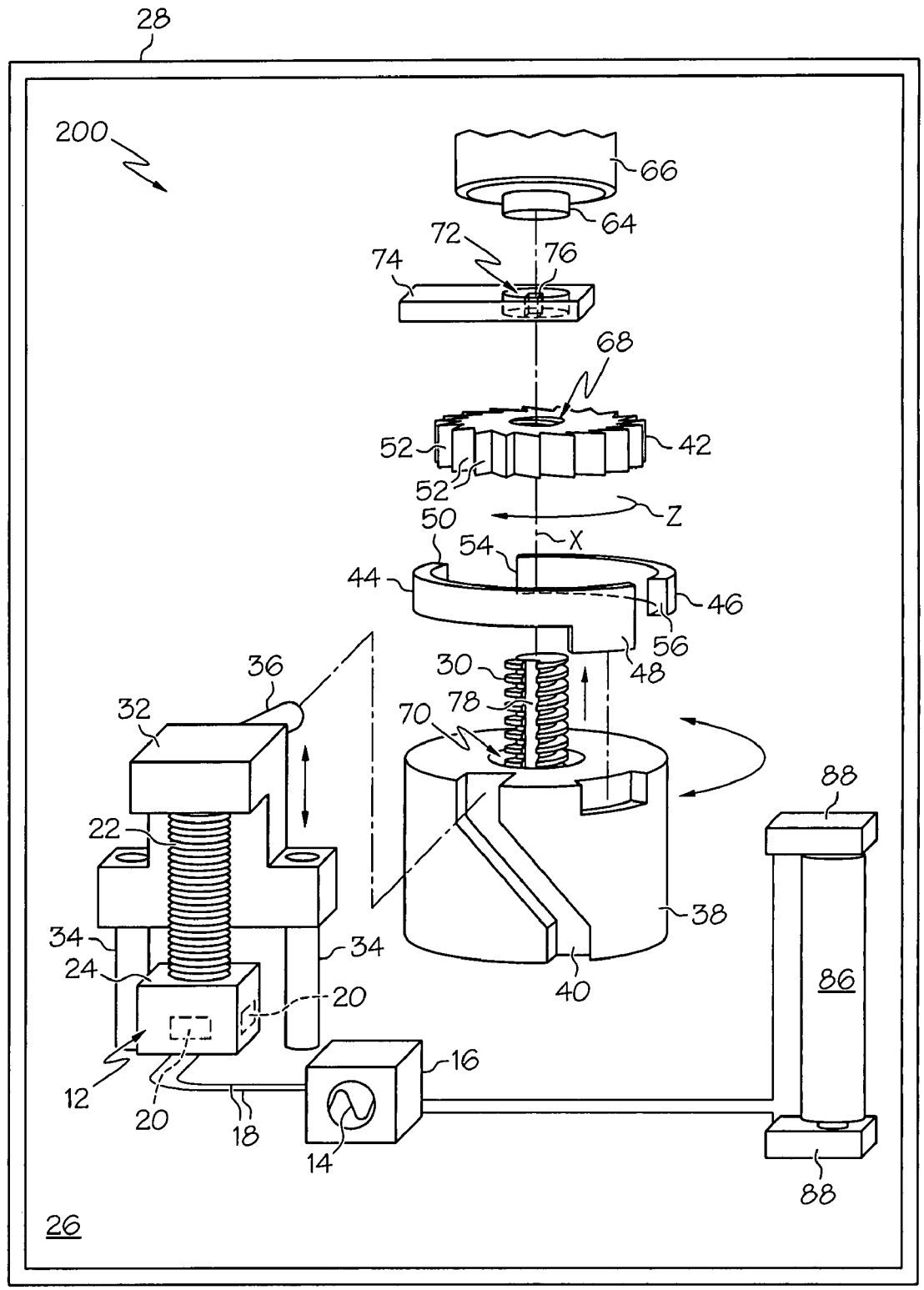
FIG. 2 is an exploded perspective view of another drug delivery pump drive embodiment using a linear piezoelectric motor positioned parallel to an axis of rotation of a lead screw arrangement according to the present invention.

FIG. 2 shows another embodiment of a pump drive 200 according to the present invention wherein the lead screw 30 and the ratchet wheel 42 are not fixed together as in the previous embodiment illustrated by FIG. 1. In this alternative embodiment, the ratchet wheel 42 provides a threaded nut portion 68 which rotates about the lead screw 30. The cam 38 provides a cavity 70 which accommodates a first portion of the lead screw 30. A second portion of the lead screw 30 extends from the cavity 70 through the threaded nut portion 68 of the ratchet wheel 42, and through a through bore or cavity 72 in a retainer 74. The retainer 74 serves to constrain the ratchet wheel 42 from translating up the rotational axis X as it rotates the threaded nut portion 68 about the lead screw 30. The retainer 74 also provides a key portion 76 situated in the cavity 72. The key portion 76 rides in a keyway 78 provided in the lead screw 30. In this manner, the lead screw 30 is constrained to translate, but not rotate incrementally, along rotational axis X. The incremental advancement of the lead screw 30 along the rotational axis X with each tooth-by-tooth rotation of the ratchet wheel 42 causes the piston 64 to be pushed into the container 66, thereby expelling the liquid drug from the container 66 in a controlled manner.

Figure 3:
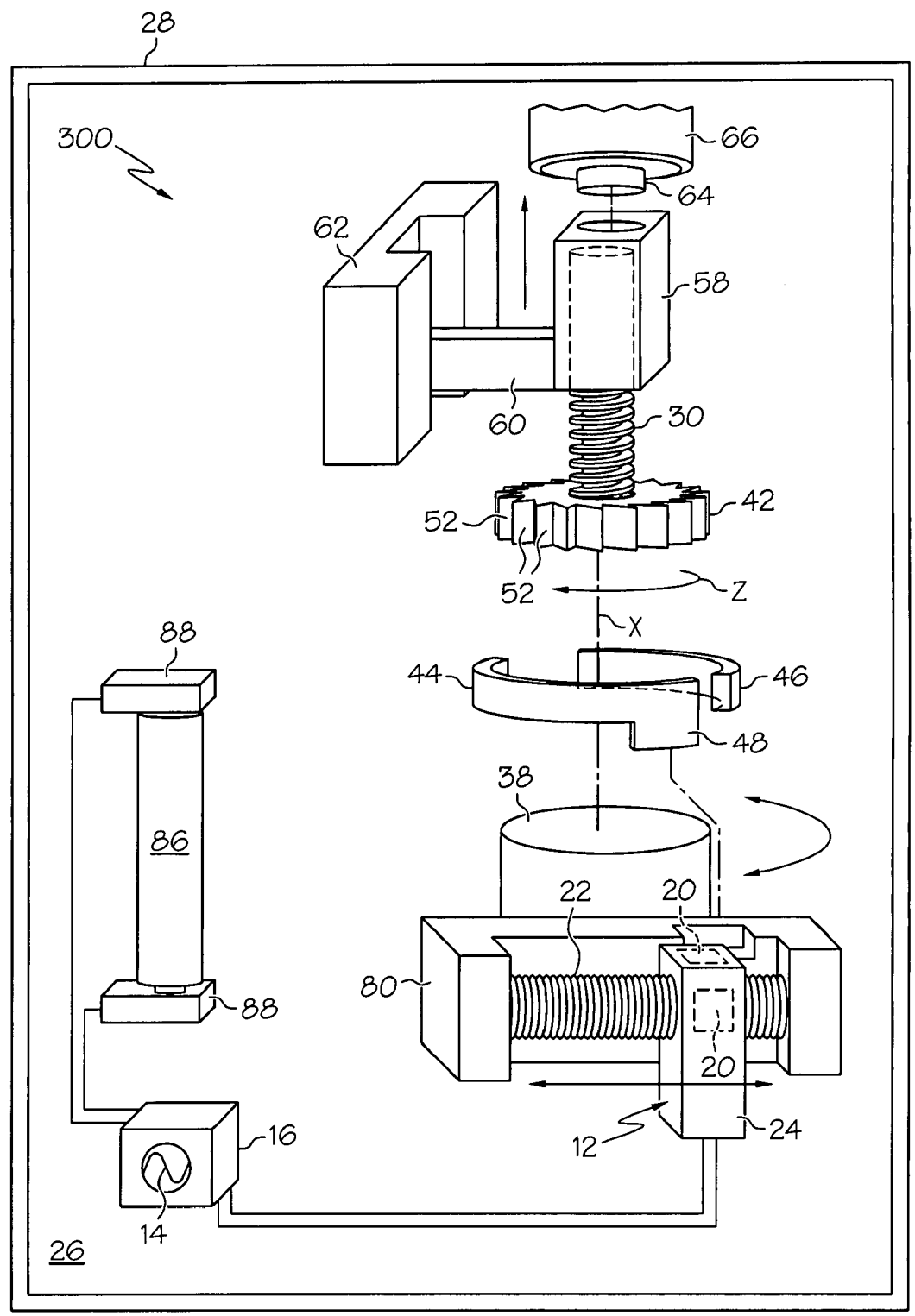
FIG. 3 is an exploded perspective view of a drug delivery pump drive embodiment using a linear piezoelectric motor positioned perpendicular to an axis of rotation of a lead screw arrangement according to the present invention.

FIG. 3 shows still another embodiment of a pump drive 300 according to the present invention. In this embodiment, the shaft 22 of the motor 12 is mounted perpendicular to the rotational axis X. The motor body 24 is mounted to the base 26 and supports the shaft 22 above the base 26. The shaft 22 is mounted between opposing tabs on the rocker 80 above the base 26. Accordingly, the motor 12 drives and rotates the rocker 80 in both directions (e.g., right and left) around the rotational axis X.

The rocker 80 mounts the first pawl 44 such that as the motor 12 oscillates the rocker 80 back and forth around the rotational axis X, the first pawl 44 rotates the ratchet wheel 42 in the advancing direction Z. The second pawl 46 is mounted or otherwise fixed to the base 26 such that the ratchet wheel 42 cannot rotate in the direction opposite to the advancing direction Z. In this embodiment, the lead screw 30 is fixed to rotate with the ratchet wheel 42. It is to be appreciated that in another embodiment, the lead screw 30 and ratchet wheel 42 may be a unitary piece. For brevity, as the pump drive 300 advances the piston 64 in the same manner as described above with reference to the pump drive 100 shown by FIG. 1, no further discussion is provided about this embodiment.

Figure 4:
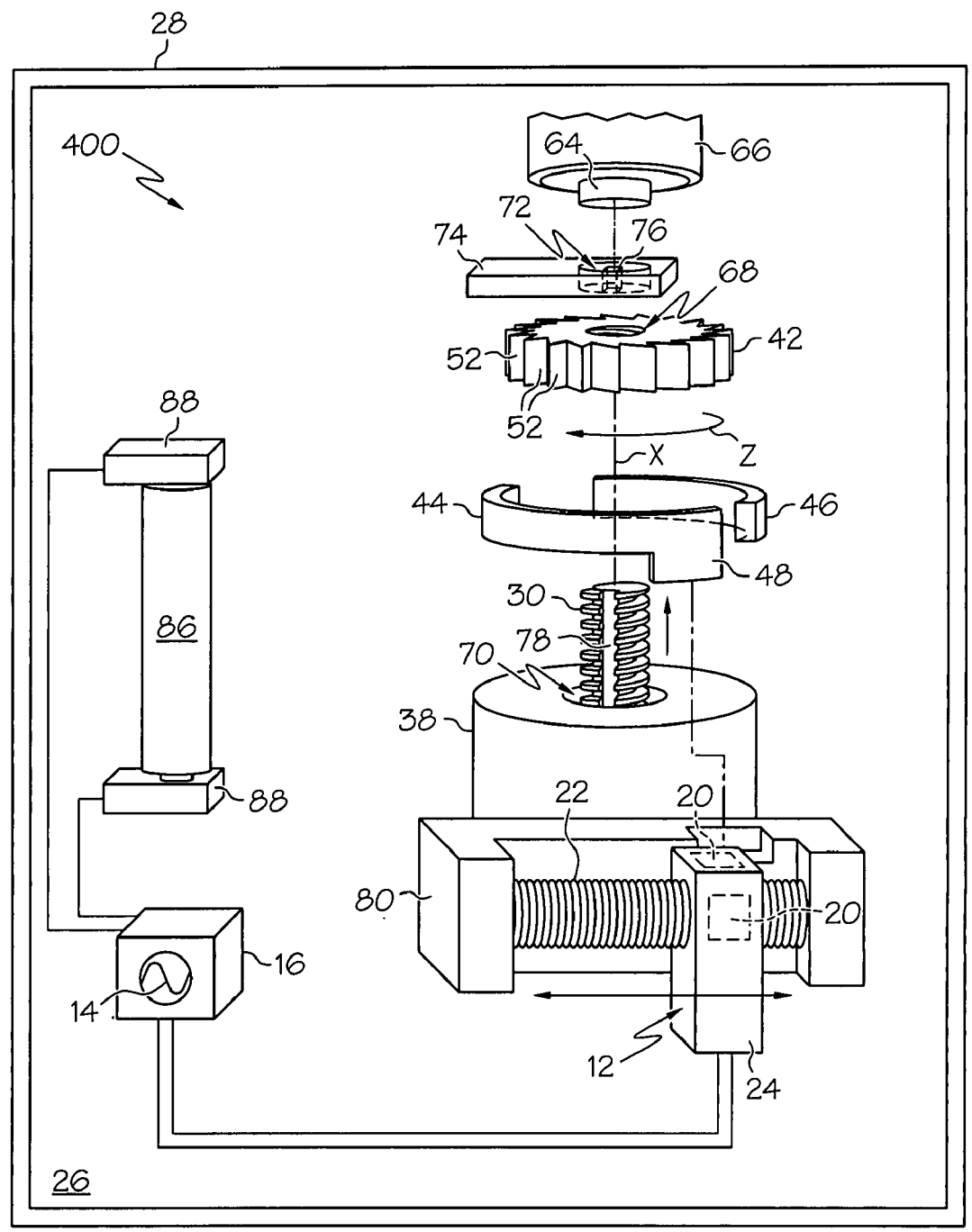
FIG. 4 is an exploded perspective view of another drug delivery pump drive embodiment using a linear piezoelectric motor positioned perpendicular to an axis of rotation of a lead screw arrangement according to the present invention.

Another embodiment of a pump drive 400 is shown by FIG. 4, with the shaft 22 of the motor 12 mounted perpendicular to the rotational axis X. In this embodiment, as in the illustrated embodiment of FIG. 2, the lead screw 30 is configured to translate about the rotational axis X but is constrained to rotate as mentioned previously in an above section. It is to be appreciated that in another embodiment, pawl 44 and rocker 80 may be a unitary piece. For brevity, as the pump drive 400 advances the piston 64 in the same manner as described above with reference to the pump drive 200 shown by FIG. 2, no further discussion is provided about this embodiment.

Figure 5:
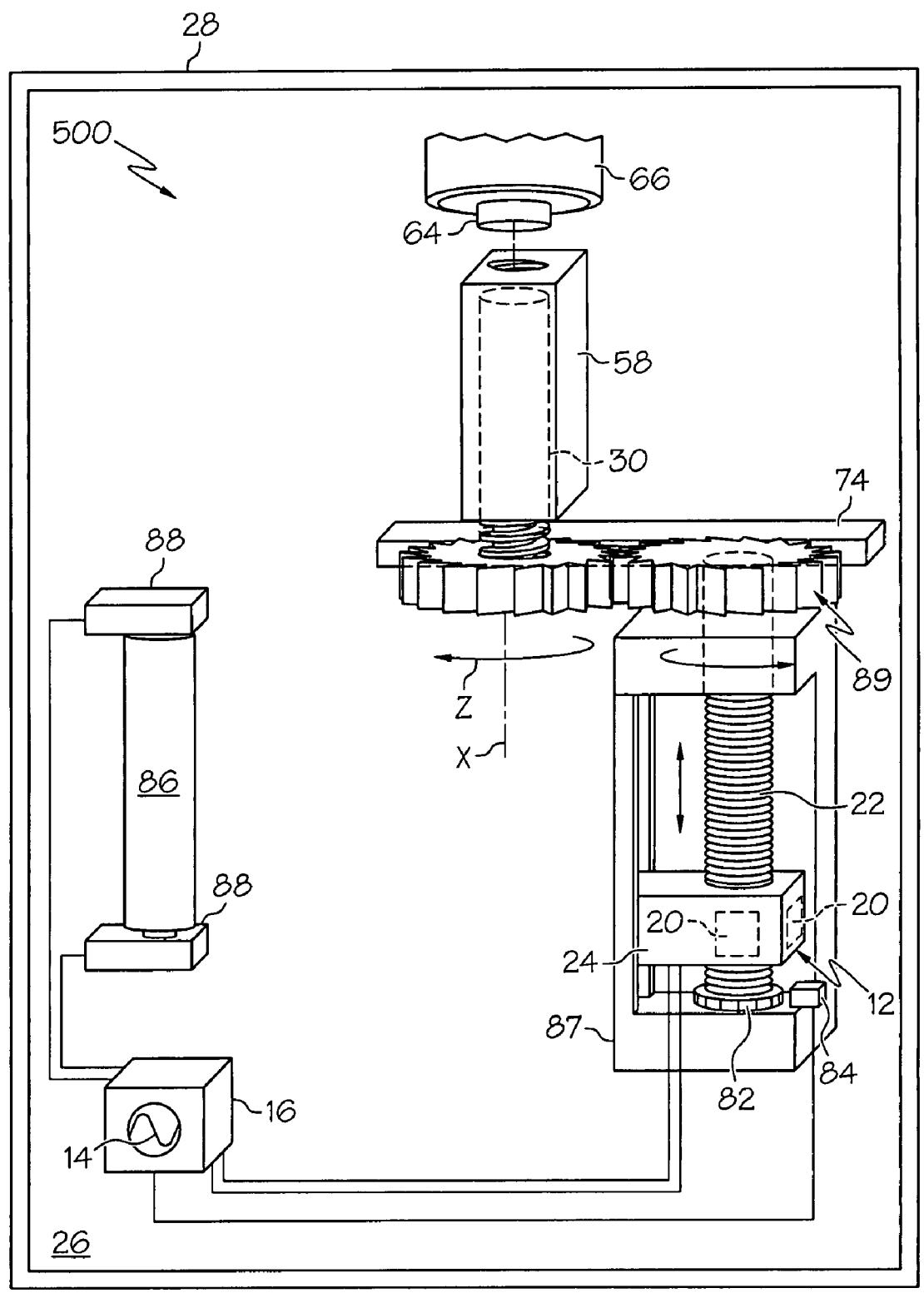
FIG. 5 is a perspective view of another drug delivery pump drive embodiment using a linear piezoelectric motor in a housing to drive a lead screw arrangement according to the present invention.

Still another embodiment of a pump drive 500 is shown by FIG. 5, which in this embodiment the shaft 22 is held to rotate but not translate by a housing 87 while the motor body 24 is allowed to translate but not rotate. The pump drive 500 further comprises the lead screw 30 having a rotational axis X and operably connected to the piston 64 via nut 58. A connection 89 between the shaft 22 and lead screw 30 transmits the rotational movement of the shaft 22 to the lead screw 30. In the illustrated embodiment, the connection 89 is a pair of gears mounted respectively to the shaft 22 and lead screw 30. In other embodiments the connection 89 between the shaft 22 and lead screw 30 may be made, for example, by a spur gear reduction set, a worm gear, and the likes, with or without a ratcheting pawl or other suitable clutching arrangement. The retainer 74 in this embodiment serves to constrain the leas screw 30, via restraining the gears of the connection 89 from translating along the rotational axis X as the lead screw 30 is rotated. Accordingly, as the motor 12 is activated, the shaft 22 outputs only rotary motion which causes the nut 58 to advance along the lead screw 30, thereby advancing the piston 64 and dispensing liquid drug from the container 66.

In the illustrated embodiment shown by FIG. 5, an encoder wheel 82 provided with markings or other features is mounted to the shaft 22 and read by an adjacent encoder 84. In this manner, the encoder 84 tracks the revolutions of the shaft 22 and hence movement of nut 58, and provides the controller 16 with the revolution information such that the motor 12 is regulated to dispense only a desired amount of the drug from the container 66. In other pump drive embodiments, the encoder wheel 82 (or markings) and encoder 84 may be placed on and provided adjacent, respectively, any other moving component of the infusion pump 28 which can provide an indication of the amount of liquid drug dispensed from the container 66, such as for example, the motor body 24, the lead screw 30, a component of connection 89, or piston 64.

In all the illustrative pump drive embodiments shown by FIGS. 1-5, a battery 86 is provided to power the infusion pump 28. The battery 86 is held between a pair of electrical terminal posts 88 which are wired to provide power to the controller 16. Other electrical component, such as for example, an on/off button 90 (FIG. 6) and a small/large dose selection switch 92 (FIG. 6) may also be provided as input to the controller 16 to provide the stated function to the infusion pump 28.

Figure 6:
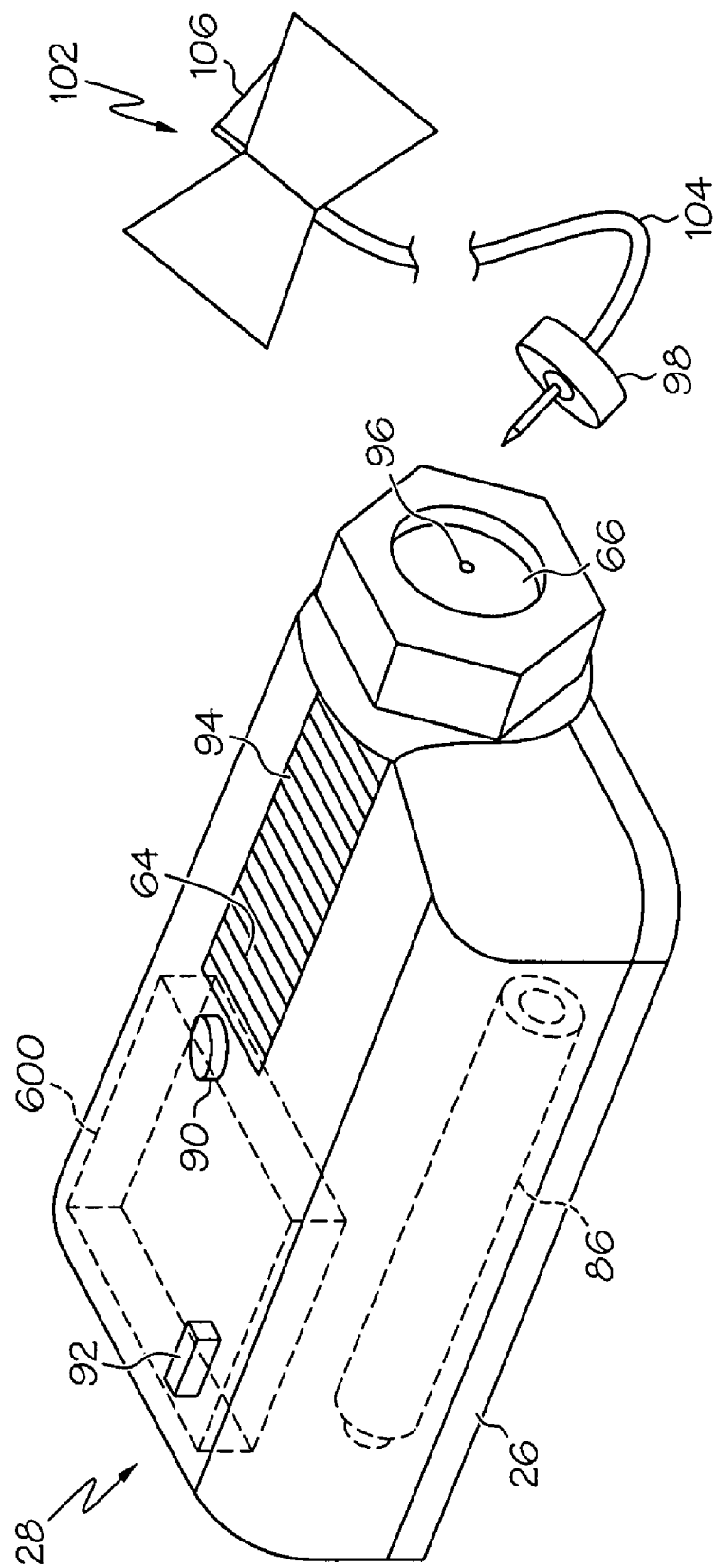
FIG. 6 is a perspective view of a miniature drug delivery pump embodiment using a drug delivery pump drive using a linear piezoelectric motor to advance a syringe piston to deliver a liquid drug according to the present invention.

As shown by FIG. 6, a pump drive 600 according to any one of embodiments of the pump drive 100, 200, 300, 400, and 500 shown by FIGS. 1-5, is conveniently used in a miniature drug delivery pump 128. In the illustrated embodiment, the battery 86 is a size AAAA, which is about 42.5 mm long and about 8.3 mm in diameter, weighing around 6.5 grams. Output of alkaline batteries in this size is about 1.5 volts, 625 mA·h. Although elements in the figures may be exaggerated in portion to other components, it is to be appreciated that the approximate relative size between the drug deliver pump 128 and the battery 86 is intended to be shown in the embodiment illustrated by FIG. 6. Accordingly, as shown, the miniature drug deliver pump 128 is not much larger than the AAAA battery 86, and is in one embodiment about 61 mm long, about 32 mm wide, and 15.5 mm in height, and weighs about 32 grams, with the container 66 holding about 2 ml of a liquid drug. Such dimensions of the drug deliver pump 128 is about one third the size of existing conventional drug deliver pumps. The small size of the drug delivery pump 128 due to the reduction in size and components of the pump drive 500 as well as the drive's silent operation, makes it easier for the patient to conceal the drug deliver pump under clothing.

In the illustrated embodiment shown by FIG. 6, the drug delivery pump 128 provides a scaled window 94 through which a portion of piston 64 is visible and by which the patient may use to meter/monitor the delivery of the liquid drug from the container 66. The container 66 includes an injection site 96 which is used to connect a spike connector 98 of an administration set 102 to the drug deliver pump 128. The spike connector 98 is connected to a fluid conduit 104 which at the distal end connects to a catheter 106, which enters the patient's intravenous system through the skin for delivery of the liquid drug.

Although not limited to, some of the noted advantages of the present invention are as follows: the inherent precision of the motion from the piezoelectric motor which can be used to accurately deliver very small doses (i.e., about 100 mL), nearly silent operation, fewer moving parts, and smaller parts. Such advantages result in an overall compact and low cost drug delivery pump for the consumer.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art.

What is claimed is:

1. A drive system used to dispense a liquid drug from a drug container having a piston, said drive system comprising:
    a lead screw having a rotational axis and operably connected to the piston;
    a ratchet wheel provided along the rotational axis and operably connected to the lead screw to move the lead screw;
    a piezoelectric motor having a shaft, a nut engaging the shaft, and piezoelectric elements configured to produce reciprocating linear motion of the shaft relative to the nut adjacent the rotational axis, wherein the shaft of the piezoelectric motor is situated parallel to the rotational axis and is connected to a slider;
    a pawl operably connected to the shaft and engaging the ratchet wheel such that the reciprocating linear motion of the shaft is converted into unidirectional rotary motion of the ratcheted wheel about the rotational axis which moves the lead screw and advances the piston to dispense the liquid drug from the drug container; and a cam rotatably mounted about the rotational axis, the cam having a slot having at least a portion thereof provided at an angle to the rotational axis, the slider having a portion slidably mounted in the slot of the cam, and wherein the pawl has an end fixed to the cam.

2. The drive system according to claim 1, wherein the lead screw is fixed to the ratchet wheel and operably connected to the piston via a nut.

3. The drive system according to claim 1, wherein the lead screw is fixed to the ratchet wheel and operably connected to the piston via a nut, the nut having a key portion mounted slidably in a keyway of the drive system such that the nut is able to translate relative to the lead screw but not rotate.

4. A drive system used to dispense a liquid drug from a drug container having a piston, said drive system comprising:
- a lead screw having a rotational axis and operably connected to the piston;
- a ratchet wheel provided along the rotational axis and operably connected to the lead screw to move the lead screw, wherein the lead screw is fixed to the ratchet wheel and operably connected to the piston via a nut, the nut comprising a key portion mounted slidably in a keyway of the drive system such that the nut is able to translate relative to the lead screw but not rotate;
- a piezoelectric motor having a shaft, a nut engaging the shaft, and piezoelectric elements configured to produce reciprocating linear motion of the shaft relative to the nut adjacent the rotational axis, wherein the shaft of the piezoelectric motor is situated parallel to the rotational axis and is connected to a slider;
- a pawl operably connected to the shaft and engaging the ratchet wheel such that the reciprocating linear motion of the shaft is converted into unidirectional rotary motion of the ratcheted wheel about the rotational axis which moves the lead screw and advances the piston to dispense the liquid drug from the drug container; and
- a cam rotatably mounted about the rotational axis, the cam having a slot having at least a portion thereof provided at an angle to the rotational axis, the slider having a portion slidably mounted in the slot of the cam, and wherein the pawl has an end fixed to the cam.

5. The drive system according to claim 1 wherein the ratchet wheel is mounted rotatably about the lead screw, and the drive system further comprises a retainer arranged to constrain the ratchet wheel from translating up the rotational axis as the ratchet wheel rotates about the lead screw.

6. The drive system according to claim 1, wherein the ratchet wheel is mounted rotatably about the lead screw, and the drive system further comprises a retainer arranged to constrain the ratchet wheel from translating up the rotational axis as the ratchet wheel rotates about the lead screw, wherein the retainer provides a through bore into which the lead screw is slidably accommodated and has a detent portion provided inside the through bore which rides in a longitudinally extending slot provided in the lead screw.

7. The drive system according to claim 1, wherein the ratchet wheel is mounted slidably about the lead screw, a fixed nut receives the lead screw and causes the lead screw to translate as it is rotated by the ratchet wheel and the lead screw is operably connected to the piston.

8. The drive system according to claim 1, wherein the ratchet wheel is mounted slidably about the lead screw.

9. The drive system according to claim 4 wherein the ratchet wheel is mounted rotatably about the lead screw, and the drive system further comprises a retainer arranged to constrain the ratchet wheel from translating up the rotational axis as the ratchet wheel rotates about the lead screw.

10. The drive system according to claim 4, wherein the ratchet wheel is mounted rotatably about the lead screw, and the drive system further comprises a retainer arranged to constrain the ratchet wheel from translating up the rotational axis as the ratchet wheel rotates about the lead screw, wherein the retainer provides a through bore into which the lead screw is slidably accommodated and has a detent portion provided inside the through bore which rides in a longitudinally extending slot provided in the lead screw.

11. The drive system according to claim 4, wherein the ratchet wheel is mounted slidably about the lead screw, a fixed nut receives the lead screw and causes the lead screw to translate as it is rotated by the ratchet wheel and the lead screw is operably connected to the piston.

12. The drive system according to claim 4, wherein the ratchet wheel is mounted slidably about the lead screw.

* * * * *

UNITED STATES PATENT AND TRADEMARK OFFICE
CERTIFICATE OF CORRECTION

| | |
|---|---|
| PATENT NO. | : 7,922,695 B2 |
| APPLICATION NO. | : 11/874417 |
| DATED | : April 12, 2011 |
| INVENTOR(S) | : Christopher Wiegel, Marco De Polo and Steven Roe |

It is certified that error appears in the above-identified patent and that said Letters Patent is hereby corrected as shown below:

Title Pg, Item (57) Abstract, last line, "resulting drug deliver pump" should read -- resulting drug delivery pump --

Col. 1, Line 36, "resulting drug deliver pump" should read -- resulting drug delivery pump --

Col. 5, Line 24, "constrain the leas" should read -- constrain the lead --

Col. 5, Line 63, "the drug deliver pump" should read -- the drug delivery pump --

Col. 5, Line 66, "the drug deliver pump" should read -- the drug delivery pump --

Col. 6, Line 3, "the drug deliver pump" should read -- the drug delivery pump --

Col. 6, Line 4, "conventional drug deliver" should read -- conventional drug delivery --

Col. 6, Line 8, "the drug deliver pump" should read -- the drug delivery pump --

Col. 6, Line 15, "the drug deliver pump" should read -- the drug delivery pump --

Signed and Sealed this
Thirteenth Day of September, 2011

David J. Kappos
*Director of the United States Patent and Trademark Office*